United States Patent [19]

Windischman

[11] 4,106,622
[45] Aug. 15, 1978

[54] TAMPER-RESISTANT RIGID SYRINGE PACKAGE AND METHOD OF MAKING THE SAME

[75] Inventor: Edward F. Windischman, Daytona Beach, Fla.

[73] Assignee: Sherwood Medical Industries Inc., St. Louis, Mo.

[21] Appl. No.: 820,674

[22] Filed: Aug. 1, 1977

[51] Int. Cl.² .................. B65D 85/20; A61M 5/00
[52] U.S. Cl. ........................... 206/365; 206/459; 215/324; 215/326
[58] Field of Search .............. 206/364, 365, 459; 215/326, 324, 317; 220/309, 310

[56] References Cited

U.S. PATENT DOCUMENTS

| | | | |
|---|---|---|---|
| 1,018,387 | 2/1912 | De Witt | 215/326 |
| 3,101,841 | 8/1963 | Baldwin | 206/459 |
| 3,107,785 | 10/1963 | Roehr | 206/365 |
| 3,272,322 | 9/1966 | Ogle | 206/365 |
| 3,673,761 | 7/1972 | Leitz | 215/324 |

Primary Examiner—William T. Dixson, Jr.
Attorney, Agent, or Firm—Stanley N. Garber; William R. O'Meara

[57] ABSTRACT

A syringe package includes a plastic cylindrical container sleeve closed at one end and open at the opposite end for receiving a sterile syringe. The sleeve has an enlarged end portion at the open end connected by a tapered portion to the main body portion of the sleeve. A rigid plastic end closure is positioned over the enlarged end portion of the sleeve and an end portion of the closure is heat-formed around the tapered portion of the sleeve so that the formed end of the cap has a smaller diameter than the enlarged portion of the sleeve. The heat-formed end portion of the closure may be provided with stress relief slots in the end portion.

25 Claims, 5 Drawing Figures

U.S. Patent
Aug. 15, 1978
4,106,622
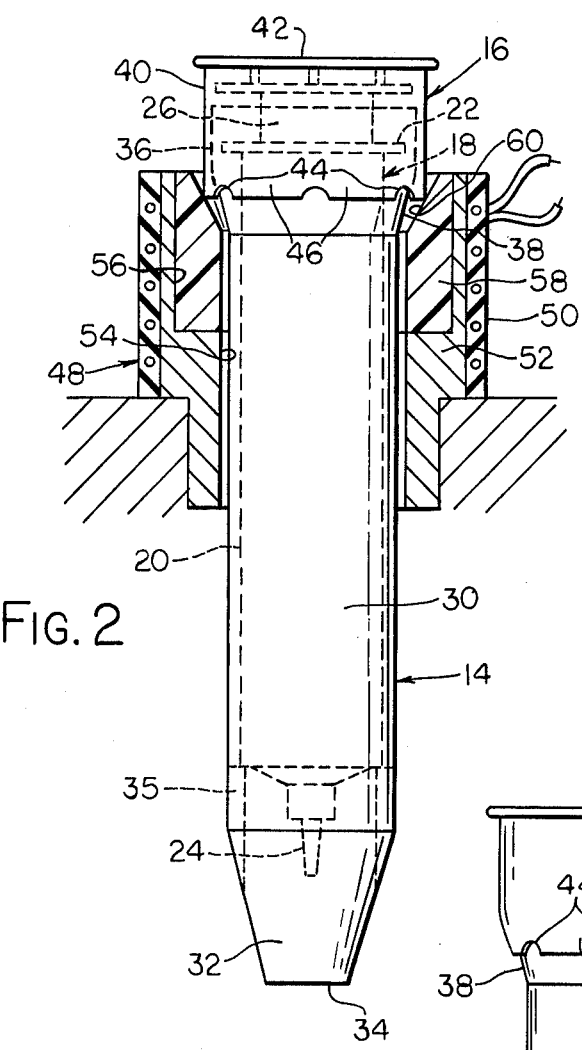
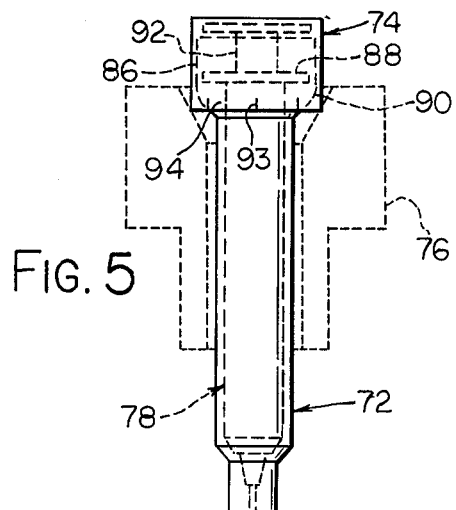
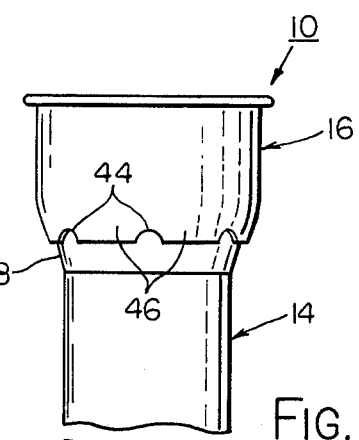
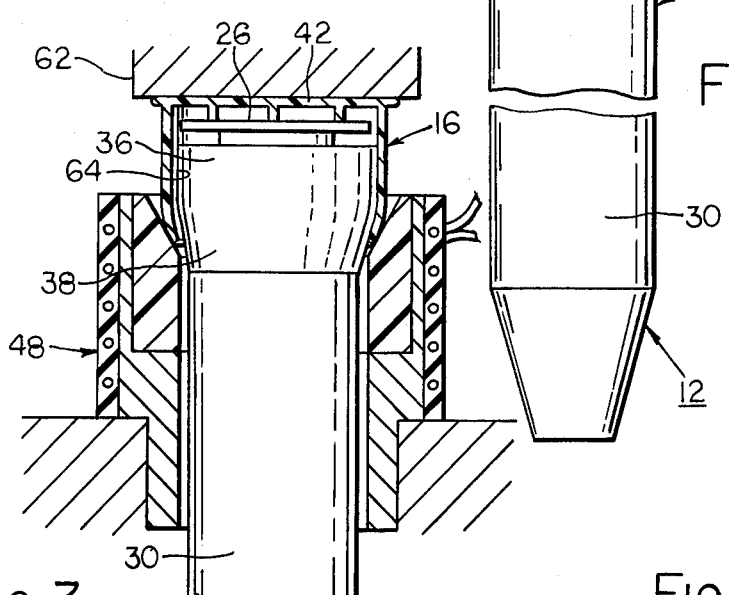
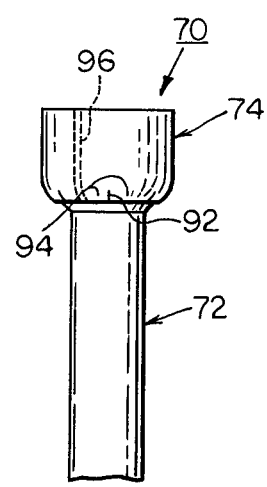

TAMPER-RESISTANT RIGID SYRINGE PACKAGE AND METHOD OF MAKING THE SAME

BACKGROUND OF THE INVENTION

This invention relates to hard packaged syringes and more particularly to tamper-resistant packages of this type.

Relatively hard plastic containers are often used to package medical syringes such as hypodermic syringes, because this type of packaging generally provides better product protection than pliable packaging, such as envelopes formed of a plastic film and the like. Hard plastic syringe packages generally include a sleeve containing the syringe and a removable closure member.

To insure that a hard packaged syringe has not been previously opened and tampered with, the removable closure member is sometimes spot-welded or thermo-welded to the sleeve. U.S. Pat. Nos. 3,820,652; 3,272,322 and 3,008,570 show packaged syringes in which closure members are fused or are otherwise spot-welded to other members of the package and which are broken when the packages are opened. In U.S. Pat. No. 3,828,775, a closure member is heat-sealed to a flange on the syringe barrel and provided with a circumferential groove that produces a weak portion that is broken to open the package. A person finding the connection formed by a spot-weld or a container part that is broken, will of course be apprised of the fact that the package may have been previously opened and that the syringe may no longer be sterile.

One of the disadvantages of the spot-welded type of tamper indicating means is that the welded area must be limited so that excessive forces are not required to open the package and, as a result, the welds sometimes inadvertently become broken during manufacture or other handling. When such packages are discovered, they are discarded as unsafe. In that type of construction where a plastic portion of the package is broken in order to open it, the package is also subject to inadvertent breakage or the package is difficult to open.

SUMMARY OF THE INVENTION

It is therefore an object of the present invention to provide a packaged syringe employing a rigid container having improved tamper-resistance means which, to a large measure, avoids the above-mentioned disadvantages.

Another object of the present invention is to provide a novel tamper-resistant, rigid packaged syringe having an end closure which is removable but greatly resists replacement, and wherein the heat fusing of parts can be avoided.

Another object is to provide an improved method of making a rigid syringe package wherein a closure member is readily applied to close the package and which is tamper-resistant.

In accordance with one form of the present invention, a syringe package is provided which includes a sleeve member receiving a syringe and having a main body portion, and an enlarged open end portion connected by a tapering portion to the main body portion. A rigid plastic closure member covers the enlarged end portion and has a lower end surrounding the tapering portion. The closure member lower end has a smaller diameter than that of the enlarged end portion. In accordance with another form of the invention, a method of making a tamper-resistant syringe package includes applying a plastic closure member to a container sleeve having a tapering portion and an enlarged end portion open at one end. The closure member has a cylindrical portion closed at one end and open at the other end. The closure member is positioned over the enlarged end portion of the sleeve with the open end portion of the enclosure member adjacent the tapering portion of the sleeve. Heat and pressure are applied to the closure member to heat-form the open end portion around the tapering portion of the sleeve.

These and other objects and advantages of the present invention will become apparent from the following detailed description and accompanying drawing.

BRIEF DESCRIPTION OF THE DRAWING

FIG. 1 is a side elevational view of a packaged syringe in accordance with a preferred embodiment of the present invention.

FIG. 2 illustrates a step in the manufacture of the packages syringe of FIG. 1;

FIG. 3 illustrates another step in the manufacture of the syringe package of FIG. 1;

FIG. 4 illustrates a fragmentary side elevational view of a syringe package of modified construction; and FIG. 5 illustrates a step in the manufacture of the packaged syringe of FIG. 4.

DESCRIPTION OF THE PREFERRED EMBODIMENT

Referring now to FIG. 1, a completed syringe package is illustrated generally at 10. The package 10 includes a rigid container 12 having a container sleeve 14 and an end closure cap 16 connected to the sleeve.

Within the container 12 is a conventional medical syringe shown in phantom at 18 in FIG. 2 which may be, for example, of the type used in injecting medicaments into the vein of a patient. Syringe 18 has a barrel 20 with a radial finger flange 22 at the upper or proximal end, and a luer tapered connector 24 at the distal or bottom end adapted for connection with a complementary luer tapered connector of a hypodermic needle (not shown). A conventional syringe piston member 26 having a piston rod and rubber piston is disposed in the syringe barrel 20.

The container sleeve 14 includes a cylindrical main body portion 30 having a tapered bottom end portion 32 encircling the luer connector 24 of barrel 20 and an integral flat bottom wall 34 closing the bottom end of the sleeve. The sleeve 14 is provided with a plurality of internal ribs 35 which engage and space the syringe from the bottom of the sleeve. As best seen in FIG. 3, the sleeve 14 has an open, enlarged, cylindrical upper end portion 36 having a greater diameter than that of the main body portion 30. Upper end portion 36 is integrally connected to the main body portion 30 by a radially inwardly tapering neck or connecting portion 38.

The enclosure cap 16, as seen in FIG. 2 before it is securely applied to the sleeve 30, includes a cylindrical portion 40 open at the bottom end and closed at the top by a flat disc-like upper end wall 42. The lower end portion of cap 16 is provided with a plurality of circumferentially spaced, stress relief slots 44 forming axially extending, resilient fingers 46 disposed around the cap. The cap, as well as the sleeve 30, are made of a suitable plastic material which is relatively hard or rigid, for example, they may be molded of polypropylene. The side walls of cap 16 are molded so that the lower end portion adjacent the open end is thinner, as seen in FIG.

3, so that the lower end of the cap is resilient enough to permit removal of the cap for opening the package, as will be discussed hereafter.

The enclosure cap 16 is applied to the sleeve 30 to close container 12 by heat-forming it about the enlarged open end portion 36 of the sleeve. As seen in FIG. 2, the sleeve 30, with syringe 18 disposed in the sleeve, is shown inserted in a heat-forming tool 48. Forming tool 48 has an electrical heating element 50 surrounding a housing 52 of metal, such as brass, which has a through bore 54 for receiving the sleeve 30 and a counterbore 56 in the upper end portion of the housing. A ring 58, for example of Teflon, is disposed in the counterbore 56 in tight fitting, heat transfer relation with the housing 52, the ring being coaxial with the bore 54. The ring 58 has an internal surface 60 which tapers radially inwardly from the upper end to an intermediate point. The lower outer peripheral edge of the cap, as seen in FIG. 2, engages the inclined or conical wall surface 60 of the forming ring. Heat is transferred from the heating element 50 through the housing 52 and forming ring 58 to the cap 16.

With the cap at a suitable forming temperature as determined by the particular type of plastic material used, a downward force is applied to the upper end 42 of cap 16 such as by hand or by a pressure-applying tool 62 shown in FIG. 3. This applied force moves the cap and sleeve slightly downwardly relative to tool 48 so that the bottom edge of the cap 16 and fingers 46 are forced by surface 60 radially inwardly against the inclined sleeve portion 38 to tightly conform to the shape of the inclined portion 38. The sleeve and cap 16 are removed from the heating tool 48 and allowed to cool so that the cap hardens to its new configuration. The cap 16 now has a permanent shape with the lower end below the enlarged portion of the sleeve 14 and having a smaller diameter than the enlarged sleeve portion as seen in FIGS. 1 and 3. The stress relief slots 44 allow the bottom end of the closure cap to conform to the tapered sleeve portion 38 without undesirable deformations and also increase the flexibility of the cap at its lower end.

The removed completed rigid container enclosing the syringe 18 provides a rigid syringe package which is now sterilized. For example, the packaged syringe 10 is subjected to a conventional sterilizing gas in a vacuum chamber for a suitable length of time to effect complete sterilization of the interior of the package. Since the closure cap 16 is tightly formed around the enlarged end portion and tapering portion of the sleeve, a breather rib 64, as seen in FIG. 3, is provided on the internal wall of the closure cap. Rib 64 extends axially from the bottom edge to the closed end of the cap and, for example, may be formed to have a radius of about 0.007 of an inch. The rib 64 maintains a small space between the cap and the enlarged sleeve portion to allow sterilization gas to enter and leave the interior of the package, thereby insuring effective sterilization.

When it is desired to open the syringe package 10 for use, the closure cap 16 may be grasped with one hand and the sleeve 14 with the other hand, and the two parts pulled axially away from each other. The forces acting on the cap under these conditions causes the resilient fingers 46 of the cap to spring radially outwardly and move axially over the enlarged end portion 36 and off of the sleeve to thereby open the rigid container 12. The syringe 18 can then be removed for use.

Once the closure cap is removed, it cannot readily be returned to reclose the sleeve 14 since resilient fingers 46 at the bottom of the cap, after forming, have a permanent set with the bottom peripheral edge of the cap having a smaller diameter than the enlarged sleeve portion 36. If the cap is replaced on the sleeve by force, it may permanently damage or stress the bottom edge or fingers of the cap to an extent that the appearance of the cap would make it obvious that the cap had been replaced.

In FIG. 4, a modified form of packaged syringe is shown at 70 including a rigid plastic sleeve 72 and a rigid plastic enclosure cap 74 closing the syringe package.

In FIG. 5, the sleeve 72 and cap 74 are shown disposed in a heat-forming tool, shown in phantom at 76, prior to the step of heat-forming the cap to the sleeve. In this case, the sleeve 72 encloses a hypodermic syringe 78 having a needle cannula 80 enclosed and protected by a needle sheath portion 82 of the sleeve 72. The lower end of sheath portion 82 is closed by a flat integral end wall 84. The sleeve 72 may be of the type shown in U.S. Pat. No. 3,008,570. That is, the main body portion of the sleeve may have an open bottom end which receives and is closed by the sheath portion 82. In such a construction, the sheath portion 82 is movable upwardly relative to the main body portion of the sleeve to assist in raising the syringe upwardly and out of the upper open end of the sleeve when it is desired to use the syringe. The upper end of the sleeve 72 is open and has an upper enlarged portion 86 which receives the radial finger flange 88 of the syringe 78. The enlarged portion 86 is connected by a neck or tapered portion 90 to the main body portion of the sleeve. The syringe has a piston and piston rod assembly 92 disposed in the barrel of the syringe.

The closure cap 74 may be heat-formed about the upper end portion 86 and tapered portion 90 of sleeve 72 in the same manner that cap 16 is formed about sleeve 14 in the embodiment illustrated in FIGS. 1–4. Also, the forming tool 76 may be identical to tool 48. For example, after the closure cap 74 has been heated to a relatively soft condition, a force is applied to the cap to move it and the sleeve 72 downwardly further into the conical portion of the heat-forming device 76 to cause the lower end portion of the cap to move radially inwardly and tightly conform to the inclined surface of the conical or tapered sleeve portion 90. The closed packaged syringe 70 is removed from the heating tool 76 and, after cooling, may be sterilized in a vacuum chamber by use of a sterilizing gas.

The cap 74 is shown provided with a plurality of circumferentially disposed axially extending stress relief slots 93 which form resilient fingers 94. For example, six slots 93 equally spaced around the cap at the periphery may be used. The wall thickness of the fingers may be less than the other portions of the closure cap to provide a desired flexibility for opening the package.

When it is desired to open the hard syringe package 70, the cap is grasped in one hand and the sleeve in the other and the two are pulled apart. With opposed axial forces applied in this manner, the fingers 94 move radially outwardly and slide off the enlarged portion of the sleeve.

Because the resilient fingers 94 have now been given a permanent set with the bottom open periphery of the cap having a substantially smaller diameter than the diameter of the enlarged portion 86 of the sleeve, the cap is not readily replaced onto the sleeve 72. In many cases, one or more of the individual fingers will be obviously deformed before the cap can be replaced on the sleeve.

If desired, a spot-welding may be effected between the cap and the enlarged portion of the sleeve to even further assure the user that the package has not been previously opened.

In FIG. 4, an axially extending breather ridge or rib 96 on the interior wall of cap 74 extends from the bottom end to the closed upper end of the cap. This rib permits the flow of sterilizing gas into and out of package 70 during sterilization of the package. Where desired, a breather rib may be formed on the sleeve in addition to or in place of a rib on the cap portion of the package.

As various changes could be made in the above construction without departing from the scope of the invention, it is intended that all material contained in the above description or shown in the accompanying drawing shall be interpreted as illustrative and not in a limiting sense.

What is claimed is:

1. A rigid syringe package comprising a rigid sleeve member closed at one end and open at the other end, a syringe in said sleeve member having a barrel with a radial flange at the proximal end thereof, and piston means in said barrel, said sleeve member having a main body portion, an enlarged end portion at said other end having a greater diameter than said body portion, and a radially inwardly tapering connection portion connecting said enlarged end portion with said body portion, and a substantially rigid plastic closure member for closing said other end of said sleeve member, said closure member being closed at one end and open at the opposite end and including a generally cylindrical portion surrounding said enlarged end portion of said sleeve member, and a radially inwardly tapering end portion connected to said cylindrical portion at said opposite end and surrounding and engaging said tapering connection portion, said end portion of said closure member being sufficiently resilient to permit manual removal of said closure member from said sleeve member and having a diameter smaller than that of said enlarged end portion of said sleeve member to thereby resist the replacement thereof on said sleeve member.

2. The package of claim 1 wherein said closure member circumferentially substantially sealingly engages a portion of said sleeve, and one of said members has spacer means thereon engaging the other of said members to space said members and allow the ingress and egress of sterilizing gas into and out of the package during sterilization of the package.

3. The package of claim 2 wherein said spacer means comprises a rib on the interior side wall of said closure member.

4. The package of claim 2 wherein said rib extends axially substantially the axial length of the side wall of said closure member.

5. The package of claim 2 wherein said end portion of said closure member has stress relief means formed therein.

6. The package of claim 1 wherein the thickness of the side walls of said tapering end portion of said closure member is less than that of other portions of said closure member.

7. The package of claim 1 wherein said closure member is formed of a thermoplastic material, and said end portion of said closure member is heat-formed in position on said sleeve member, the greatest lateral dimension of said enlarged end portion being greater than the greatest lateral dimension of said body portion.

8. The package of claim 1 wherein said end portion of said closure member has stress relief means formed therein.

9. The package of claim 8 wherein said stress relief means includes a plurality of circumferentially spaced recesses in the side wall of said closure member at said opposite end.

10. The package of claim 9 wherein said stress relief means includes a plurality of circumferentially spaced slots in the side wall of said closure member extending from said opposite end a predetermined distance toward said closed end.

11. The package of claim 8 wherein said sleeve member is of relatively rigid plastic and includes spacer means between said sleeve member and said closer member to allow sterilization gas to flow into the package to sterilize the syringe therein.

12. The package of claim 1 wherein said tapering end portion of said closure member extends substantially entirely around said sleeve member.

13. The package of claim 1 wherein said tapering connection portion of said sleeve member extends entirely around said sleeve member and has a taper at an angle to the major portion of said body portion.

14. The package of claim 13 wherein the taper of said tapering end portion of said closure member substantially conforms to the taper of said tapering connection portion of said sleeve member.

15. The package of claim 14 wherein said tapering end portion of said closure member extends substantially entirely around said sleeve member.

16. The package of claim 15 further including spacer means between said members to provide a space for allowing the flow of sterilizing gas from the exterior of the package into the interior of the package during sterilization of the interior of the package.

17. The package of claim 1 wherein said enlarged end portion surrounds said radial flange of said syringe.

18. The method of making a tamper resistant rigid syringe package comprising the steps of providing a rigid syringe sleeve closed at one end and open at the other end and having a main body portion, an enlarged end portion at said other end having a greater diameter than said body portion, and a tapering portion connecting said enlarged end portion with said body portion, positioning a syringe having an enlarged end part in said sleeve with the enlarged part said enlarged end portion of the sleeve, providing a rigid closure member of thermoplastic material having a cylindrical body open at one end and having an end wall closing the opposite end, the cylindrical body having an axial length greater than that of the enlarged end portion of the sleeve, positioning the closure member over the enlarged end portion of the sleeve with an end portion of the closure member at the open end thereof surrounding a portion of the tapering portion of the sleeve, applying heat and radially inward pressure to the end portion of the closure member to soften the same and form it against the tapering portion of the sleeve, and cooling the formed closure member.

19. The method of claim 18 wherein said step of applying heat and pressure includes inserting the sleeve and closure member into a heat-forming tool with the open end portion of the closure member engaging a tapered surface of the tool, heating the open end portion of the closure member to soften it, applying an axial force to the exterior of the closure member after it is softened to move the closure member and a sleeve further into the tool and cause the end portion thereof to be moved inwardly by the tapered surface against the tapering portion of the sleeve.

20. The method of claim 19 wherein said tapered surface of the tool extends continuously around said end portion of the closure member when the sleeve and closure member are inserted into the tool.

21. The method of claim 18 providing pressure relief slots at the open end of the closure member.

22. The method of claim 18 wherein the step of providing the closure member includes molding the closure member such that the open end portion thereof has a wall thickness less than that of other portions thereof so that after forming and cooling the open end portion of the closure member is resilient enough to permit removal of the closure member from the sleeve.

23. A packaged syringe comprising a substantially rigid container, and a sterile syringe disposed in and maintained sterile by said container, said container including a relatively rigid sleeve having a longitudinally extending main body portion closed at one end and having a major portion thereof of substantially constant diameter, an enlarged portion having one end open and having a diameter greater than that of said major portion, and a radially inwardly extending portion extending continuously around said sleeve member and extending angularly relative to said major portion connecting the opposite ends of said body and enlarged portions together, and a closure cap of relatively rigid material having one end closed and the opposite end open and including a main portion extending longitudinally between said closed and open ends thereof and surrounding said enlarged portion of said sleeve, said cap having a resilient peripheral end portion adjacent said open end thereof extending radially inwardly and closely surrounding and engaging said radially inwardly extending portion of said sleeve so that said cap end portion bends radially outwardly upon the application of a manual force sufficient to pull said cap and sleeve apart when opening said container and bends inwardly upon removal from said sleeve due to the resiliency thereof so that it presents an interference to the replacement of said cap on said sleeve member.

24. The packaged syringe of claim 23 wherein said sleeve and said cap are of flexible plastic material.

25. The packaged syringe of claim 24 wherein said peripheral end portion of said cap has stress relief means increasing the flexibility thereof.

* * * * *